US00PP11440P

United States Patent [19]

Trees

[11] Patent Number: Plant 11,440

[45] Date of Patent: Jul. 11, 2000

[54] GERANIUM PLANT NAMED 'BFP-1697'

[75] Inventor: Scott C. Trees, Nipomo, Calif.

[73] Assignee: Ball Floraplant a division of Ball Horticultural Co., West Chicago, Ill.

[21] Appl. No.: 09/114,055

[22] Filed: Jul. 10, 1998

[51] Int. Cl.[7] ..... A01H 5/00

[52] U.S. Cl. ..... Plt./329

[58] Field of Search ..... Plt./325, 329

[56] References Cited

U.S. PATENT DOCUMENTS

P.P. 9,217 7/1995 Trees ..... Plt./329

P.P. 9,589 6/1996 Trees ..... Plt./325

P.P. 11,075 10/1999 Hanes ..... Plt./329

*Primary Examiner*—Howard J. Locker

*Assistant Examiner*—Kent L. Bell

*Attorney, Agent, or Firm*—C. A. Whealy

[57] ABSTRACT

A new and distinct cultivar of Geranium plant named 'BFP-1697', characterized by its numerous semi-double purple-colored flowers with white centers; upright and rounded growth habit; vigorous and basal branching; and medium green leaves.

1 Drawing Sheet

BACKGROUND OF THE INVENTION

The present invention relates to a new and distinct cultivar of Geranium plant, botanically known as *Pelargonium*× *hortorum*, and hereinafter referred to by the cultivar name 'BFP-1697'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the proprietary *Pelargonium*×*hortorum* selection 8410 as the male, or pollen parent, with the proprietary *Pelargonium*×*hortorum* selection 690 as the female, or seed parent. The cultivar 'BFP-1697' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1697'. These characteristics in combination distinguish 'BFP-1697' as a new and distinct cultivar:

1. Numerous semi-double purple-colored flowers with white centers.

2. Upright and rounded growth habit.

3. Vigorous and basal branching.

4. Medium green leaves.

The new Geranium can be compared to the cultivar, 'Fox' (disclosed in U.S. Plant Pat. No. 7,083). However, in side-by-side comparisons conducted by the Inventor in Arroyo Grande, Calif., plants of the new Geranium differ from plants of the cultivar 'Fox' in the following characteristics:

1. Plants of the new Geranium are more freely branching than plants of the cultivar 'Fox'.

2. Plants of the new Geranium have much shorter lateral branches than plants of the cultivar 'Fox'.

3. Plants of the new Geranium have shorter leaves and fewer leaves per lateral branch than plants of the cultivar 'Fox'.

4. Leaves of the new Geranium do not have a discernible zonation pattern whereas leaves of plants of the cultivar 'Fox' do have a discernible zonation pattern.

5. Flower umbels of plants of the new Geranium are smaller and have smaller flowers than flower umbels of plants of the cultivar 'Fox'.

6. Flower color of plants of the new Geranium is deeper purple than flower color of plants of the cultivar 'Fox'.

7. Plants of the new Geranium have longer peduncles than plants of the cultivar 'Fox'.

A detailed comparison of plants of the cultivar 'BFP-1697' and the cultivar 'Fox' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a top perspective view of a typical plant of 'BFP-1697'. Flower and foliage colors in the photograph may appear different from the actual colors due to light reflectance.

DETAILED BOTANICAL DESCRIPTION

The cultivar 'BFP-1697' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar 'BFP-1697'.

Parentage:

*Male parent.*—Proprietary *Pelargonium×hortorum* selection 8410.

*Female parent.*—Proprietary *Pelargonium×hortorum* selection 690.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous and freely branching.

Plant description:

*General appearance.*—Upright and rounded growth habit, vigorous. Appropriate for 10 and 12.5-cm containers. About nine weeks are required to produced a finished 10-cm container from a rooted cutting.

*Growth and branching habit.*—Basally branching with about three lateral branches at the base.

*Plant height, base of plant to top of leaf plane.*—About 21 cm.

*plant width.*—About 22.6 cm.

*Lateral branches.*—Length: About 5.5 cm. Internode length: About 1.8 cm. Color: 144A.

*Foliage description.*—Leaves simple, generally symmetrical, abundant, opposite. Quantity of leaves per lateral branch: About nine. Length: About 4.7 cm. Width: About 8.8 cm. Shape: Reniform with rounded apex, cordate base, crenate and undulating margin. Texture: Dull, upper surface pubescent. Color: Fully expanded foliage, upper surface: Slightly lighter than 147A at base, 147A towards margin. Fully expanded foliage, lower surface; 147B. Venation, upper surface: 144B. Venation, lower surface: 144B. Petiole: Length: About 8.6 cm. Diameter: About 3 mm. Color: 144A.

Flower description:

*Flower type and habit.*—Purple-colored flowers. Very freely and continuously flowering. Flowers arranged in hemispherical umbels arising from apical leaf axils. Umbels displayed above or beyond the foliage. Usually about five umbels per plant. Flowers semi-double and round. Umbels persistent.

*Flowering season.*—Year-round under greenhouse conditions. In the garden, flowering is continuous from spring through summer.

*Umbels.*—Number of flowers per umbel: About 30. Diameter: About 8.9 cm. Height: About 5.5 cm.

*Flowers.*—Diameter: About 4 cm. Depth (height): About 2 cm.

*Flower buds.*—Length: About 1.5 cm. Diameter: About 9 mm. Shape: Elliptic.

*Petals.*—Quantity: About five or six petals with usually about two petaloids, overlapping. Length: About 2.1 cm. Width: About 2 cm. Shape: Obovate with rounded apex and entire margin. Texture: Smooth. Color: Fully opened, upper surface: 74A with white at base giving the flower a "white-eyed" appearance. Fully opened, lower surface: 74C. Petaloids: Irregular in shape with very narrow white, 155D, base; about 1 cm in length and about 3 mm in width; 74A in color.

*Peduncle* (*umbel stem*).—Length: About 15.2 cm. Strength: Strong. Angle: Mostly erect. Texture: Pubescent. Color: 143C overlaid with 183B becoming more red, 183B, with age.

*Pedicel* (*individual flower stem*).—Length: About 3.8 cm. Strength: Strong. Angle: Upright or outward. Texture: Pubescent. Color: 183B.

*Reproductive organs.*—Androecium: Anther size: About 1.5 mm. Amount of pollen: Moderate. Pollen color: 167A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1697' | 'FOX' |
|---|---|---|
| PLANT HEIGHT | About 21 cm | About 21 cm |
| PLANT WIDTH | About 22.6 cm | About 21 cm |
| NUMBER OF BASAL BRANCHES | About 3 | About 2 |
| LATERAL BRANCH LENGTH | About 5.5 cm | About 10 cm |
| INTERNODE LENGTH | About 1.8 cm | About 1.5 cm |
| QUANTITY OF LEAVES PER LATERAL BRANCH | About 9 | About 15 |
| LEAF LENGTH | About 4.7 cm | About 7.5 cm |
| LEAF WIDTH | About 8.8 cm | About 8.8 cm |
| LEAF COLOR, UPPER SURFACE | Slightly lighter than 147A at base, 147A towards margin | 137B, slight zonation pattern, 137A |
| UMBEL DIAMETER | About 8.9 cm | About 10 cm |
| UMBEL HEIGHT | About 5.5 cm | About 7 cm |
| FLOWER DIAMETER | About 4 cm | About 5 cm |
| QUANTITY OF PETALS/PETALOIDS PER FLOWER | About 9 | About 16 |
| PETAL COLOR, UPPER SURFACE | 74A with white base | 66A with reddish, 43A, base |
| PETAL COLOR, LOWER SURFACE | 74C | 61C |
| PEDUNCLE LENGTH | About 15.2 cm | About 13 cm |

It is claimed:

1. A new and distinct cultivar of Geranium plant named 'BFP-1697', as illustrated and described.

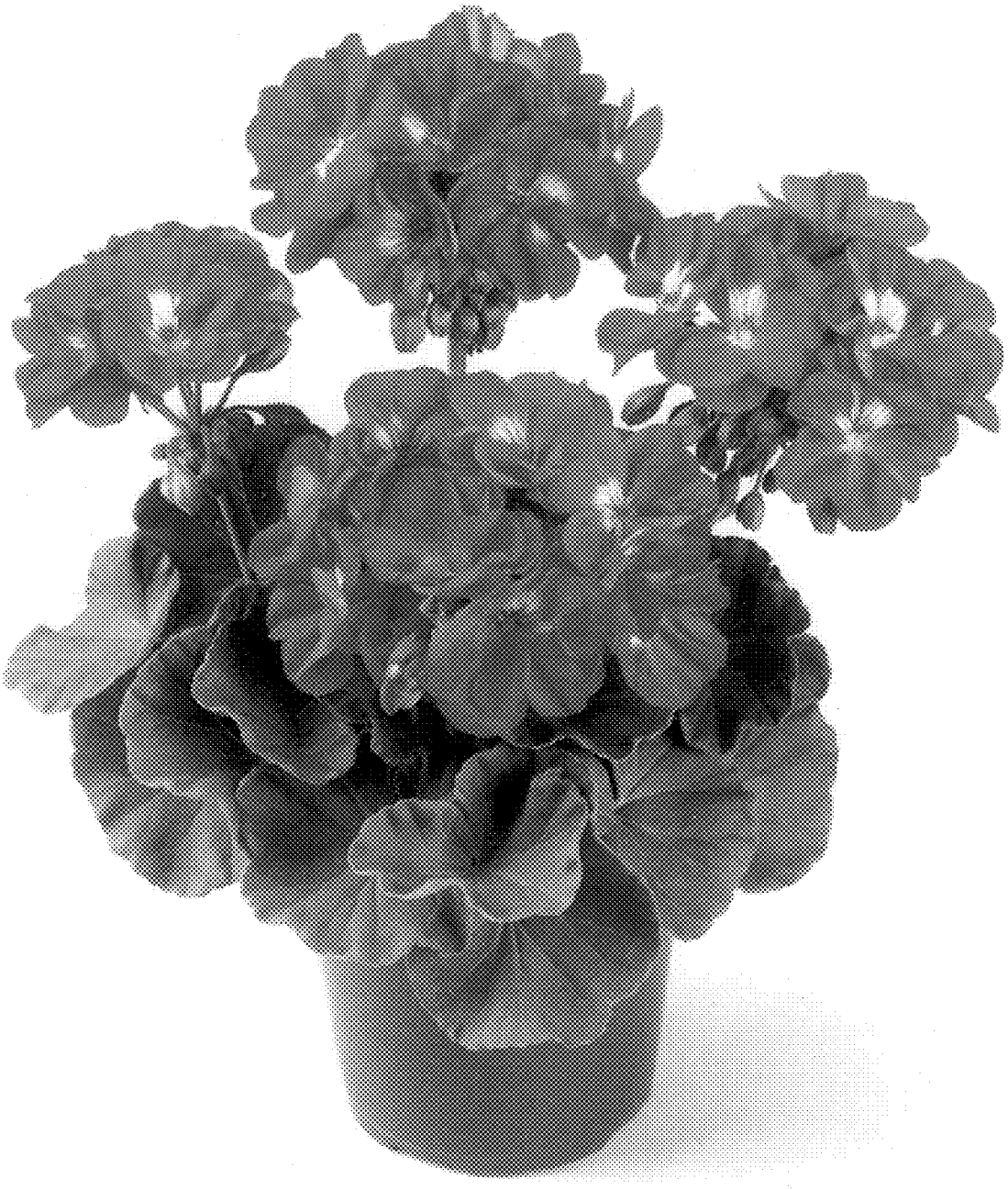

* * * * *